United States Patent
Alshwaimi et al.

(10) Patent No.: US 10,857,072 B2
(45) Date of Patent: Dec. 8, 2020

(54) DENTAL COMPOSITION AND METHOD OF DIRECT PULP CAPPING

(71) Applicant: Imam Abdulrahman bin Faisal University, Dammam (SA)

(72) Inventors: Emad Alshwaimi, Dammam (SA); Abdul Majeed, Dammam (SA); Aiman A. Ali, Dammam (SA)

(73) Assignee: Imam Abdulrahman bin Faisal University, Dammam (SA)

( * ) Notice: Subject to any disclaimer, the term of this patent is extended or adjusted under 35 U.S.C. 154(b) by 468 days.

(21) Appl. No.: 15/338,658

(22) Filed: Oct. 31, 2016

(65) Prior Publication Data
US 2018/0116915 A1  May 3, 2018

(51) Int. Cl.
| A61K 6/69 | (2020.01) |
| A61K 6/52 | (2020.01) |
| A61K 6/851 | (2020.01) |
| A61K 6/889 | (2020.01) |

(52) U.S. Cl.
CPC .......... *A61K 6/69* (2020.01); *A61K 6/52* (2020.01); *A61K 6/851* (2020.01); *A61K 6/889* (2020.01)

(58) Field of Classification Search
CPC .......... A61K 6/06; A61K 6/02; A61K 6/0067; A61K 6/0835; A61K 6/0606
USPC .................................................... 433/228.1
See application file for complete search history.

(56) References Cited

U.S. PATENT DOCUMENTS

| 8,574,604 | B2 * | 11/2013 | Esfand ...................... | A61P 9/10 424/405 |
| 9,801,792 | B2 * | 10/2017 | Primus ...................... | A61K 6/69 |
| 2004/0258723 | A1 * | 12/2004 | Singh ........................ | A61K 6/30 424/401 |
| 2005/0020720 | A1 * | 1/2005 | Dickens .................... | A61K 6/20 523/115 |
| 2005/0028705 | A1 * | 2/2005 | Wagh ....................... | C04B 28/34 106/35 |

(Continued)

FOREIGN PATENT DOCUMENTS

| BR | PI0802009 A2 | 1/2010 |
| KR | 1370023 B1 | 3/2014 |

(Continued)

OTHER PUBLICATIONS

T. Dammaschke, et al., "Mineral trioxide aggregate for direct pulp capping: a histologic comparison with calcium hydroxide in rat molars.", https://www.researchgate.net/publication/41457274_Mineral_trioxide_aggregate, vol. 41, Issue 2, Feb. 2010, pp. 20-30.

*Primary Examiner* — Yogesh P Patel
*Assistant Examiner* — Stephen R Sparks
(74) *Attorney, Agent, or Firm* — Oblon, McClelland, Maier & Neustadt, L.L.P.

(57) ABSTRACT

A method of direct pulp capping of a tooth including administering a dental composition comprising betamethasone and gentamicin onto an exposed pulp of a tooth, and covering the dental composition present on the tooth with a glass ionomer cement. The dental composition is administered in an amount effective to form a calcification over the exposed pulp. A dental composition having betamethasone, gentamicin, and optionally including a Portland cement. The dental composition is administered to an exposed pulp of a tooth to form a calcification over the exposed pulp.

10 Claims, 4 Drawing Sheets

(56) References Cited

U.S. PATENT DOCUMENTS

2011/0104644 A1* 5/2011 Primus .................. A61K 6/887
433/224
2015/0344512 A1* 12/2015 Prakash ................ B01D 15/08
536/18.1

FOREIGN PATENT DOCUMENTS

| WO | WO 2009/029049 A1 | 3/2009 | |
|----|----|----|----|
| WO | WO 2009029049 A1 * | 3/2009 | ......... A61L 24/0015 |
| WO | WO 2015/015212 A1 | 2/2015 | |

* cited by examiner

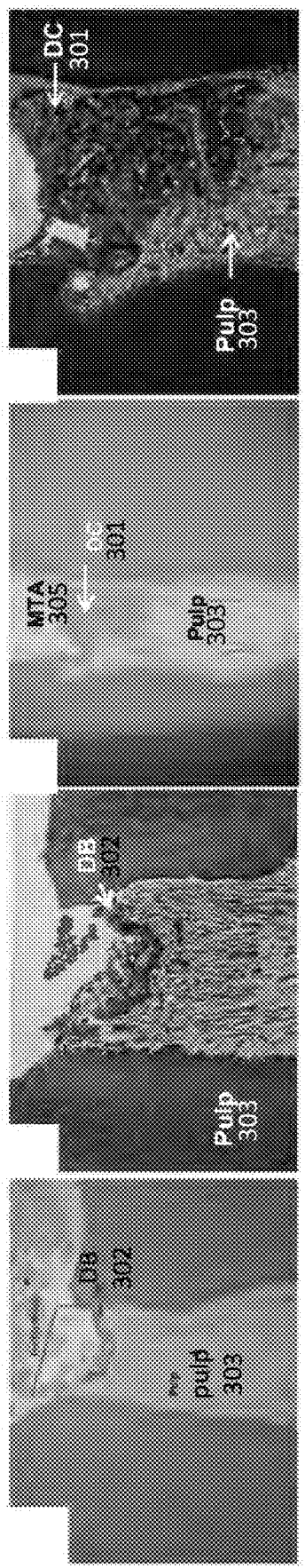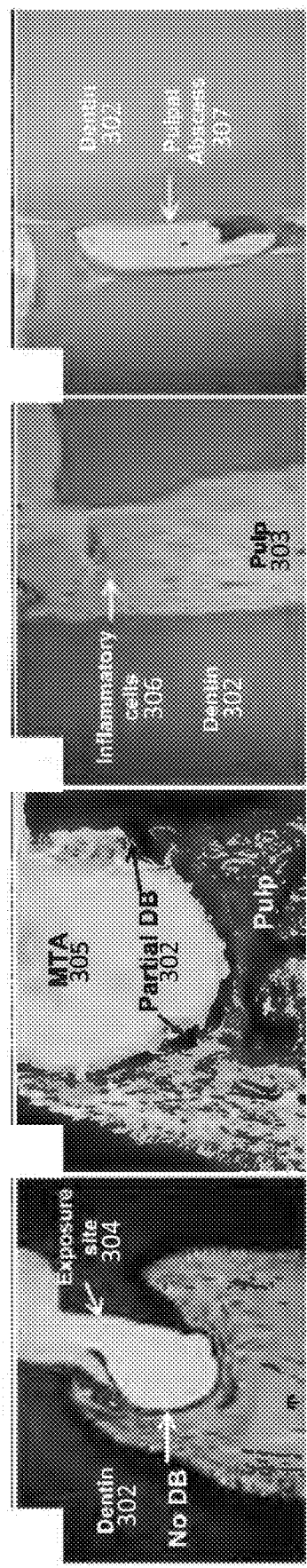

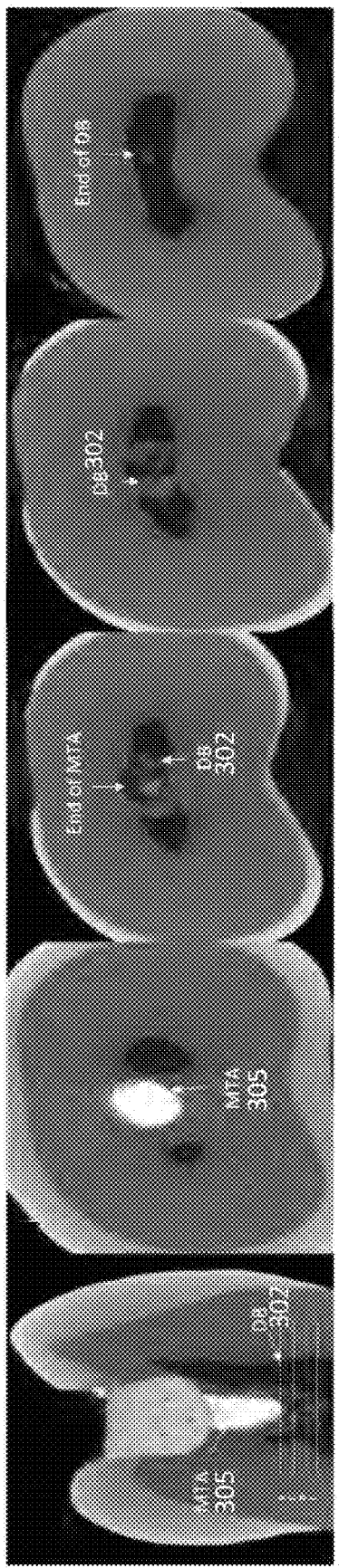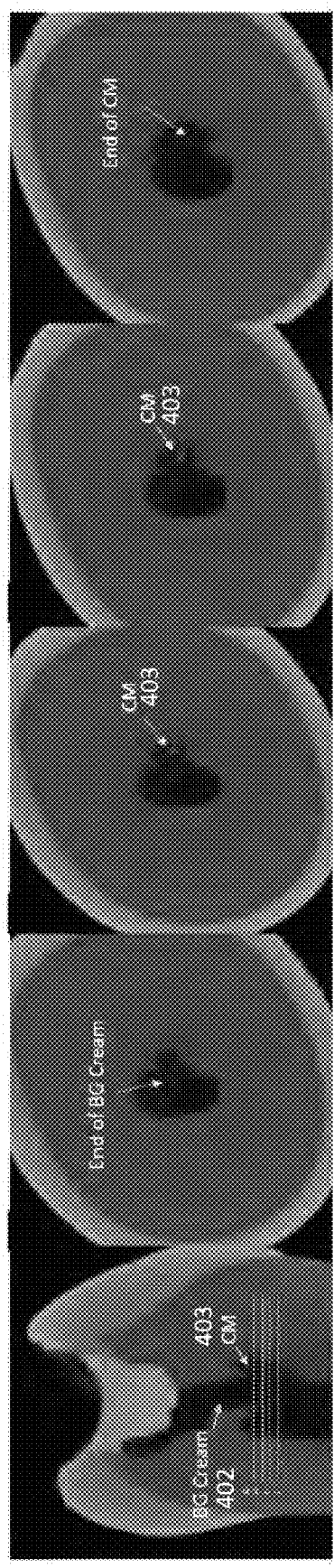

DENTAL COMPOSITION AND METHOD OF DIRECT PULP CAPPING

BACKGROUND OF THE INVENTION

Technical Field

The present invention relates to a method of administering a dental composition having betamethasone, gentamicin and, optionally, Portland cement, to a pulp exposed region of a tooth to repair and protect the pulp of the tooth by enabling the formation of a calcification, also known as a dentin bridge.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Direct pulp capping is performed to protect pulp affected by caries, trauma, or other injuries to maintain its functional and biological activities. See Asgary S, Eghbal M J, Parirokh M, et al. "A comparative study of histologic response to different pulp capping materials and a novel endodontic cement," Oral Surg Oral Med Oral Pathol Oral Radiol Endod 2008; 106:609-14. Vital pulp tissue is responsible for the formation of secondary dentin, reparative dentin, and peritubular dentin in response to different stimuli. See Al-Hiyasat A S, Barrieshi-Nusair K M, A-Omari M A. "The radiographic outcomes of direct pulp-capping procedures performed by dental students: a retrospective study," J Am Dent Assoc 2006; 137:1699-705. In direct pulp capping, a protective layer of biomaterial is placed over the exposed pulp tissue. These biomaterials should be biocompatible and bioactive, and they should possess appetite-forming ability and provide a biological seal. See Gandolfi M G, Spagnuolo G, Siboni F, et al. "Calcium silicate/calcium phosphate biphasic cements for vital pulp therapy: chemical-physical properties and human pulp cells response," Clin Oral Investing 2015; 19:2075-89. Calcium hydroxide has been a material of choice for pulp capping since 1930 because of its antibacterial activity, ability to release calcium and hydroxyl ions, and low potential for irritation of the traumatized pulp tissue. See Nowicka A. Wilk G, Lipski M, et al. "Tomographic evaluation of reparative dentin formation after direct pulp capping with Ca(OH)2, MTA, Biodentine, and dentin bonding system in human teeth," J Endod 2015; 41:1234-40; and Tziafas D, Belibasakis G, Veis A, Papadimitriou S. "Dentin regeneration in vital pulp therapy: design principles," Adv Dent Res 2001; 15:96-100. However, it has major disadvantages including high solubility, dissolution in tissue fluids, and poor sealing ability.

Calcium silicate-based materials such as mineral trioxide aggregate (MTA) have attained growing attention because compared with calcium hydroxide, they cause less pulp inflammation and form dentin bridges with significantly greater frequency and thickness. See Aeinehchi M, Eslami B, Ghanbariha M, Saffar A S. "Mineral trioxide aggregate (MTA) and calcium hydroxide as pulp-capping agents in human teeth: a preliminary report," Int Endod J 2003; 36:225-31; and Ford T R, Torabinejad M, Abedi H R, et al. "Using mineral trioxide aggregate as a pulpcapping material," J Am Dent Assoc 1996; 127:1491-4. Although clinical studies have also demonstrated that MTA results in good outcomes when used as an indirect or direct pulp-capping material, it has a delayed setting time, poor handling characteristics, and an off-white color. See Parirokh M, Torabinejad M. "Mineral trioxide aggregate: a comprehensive literature review-part III: clinical applications, drawbacks, and mechanism of action," J Endod 2010; 36:400-13; and Okiji T, Yoshiba K. "Reparative dentinogenesis induced by mineral trioxide aggregate: a review from the biological and physicochemical points of view," Int J Dent 2009; 2009:1-12.

Pulpal trauma or exposure in conjunction with a pulp-capping procedure can induce inflammation in the pulpal tissue. Pulp-capping materials containing anti-inflammatory ingredients may prevent progression to irreversible pulpitis, thus protecting the vitality of the pulp. Topical corticosteroids have known anti-inflammatory and vasoconstrictive properties. See Dyderski S, Grzeskowiak E, Szalek E. Mrzyglod A. "Pharmaceutical availability of betamethasone dipropionate and gentamicin sulfate from cream and ointment," Acta Pol Pharm 2002; 59:99-103. Direct application of corticosteroids reduces pulpal inflammation, and some corticosteroids have demonstrated better anti-inflammatory effects compared with hydrocortisone. See Fachin E V, Zaki A E. "Histology and lysosomal cytochemistry of the post-surgically inflamed dental pulp after topical application of steroids: I-histological study," J Endod 1991; 17:457-60. In a direct pulp-capping study in a rabbit model, the topical application of topical corticosteroid and an antibiotic cream significantly reduced histopathologic changes in dental pulps compared with those treated with calcium hydroxide. See Aljandan B, AlHassan H, Saghah A, et al. "The effectiveness of using different pulp capping agents on the healing response of the pulp," Indian J Dent Res 2012; 23:633-7. However, calcium hydroxide used in the aforementioned study was hard-setting cement form that might have different pulpal response compared with other forms of calcium hydroxide.

In view of the forgoing, one objective of the present invention is to provide a method of direct pulp capping of a tooth employing a topical corticosteroid, an antibiotic, and a cementing compound.

BRIEF SUMMARY OF THE INVENTION

According to a first aspect a method of direct pulp capping of a tooth including administering a dental composition comprising betamethasone and gentamicin onto an exposed pulp of the tooth and covering the dental composition present on the tooth with a glass ionomer cement. The dental composition is administered in an amount effective to form a calcification over the exposed pulp.

In some implementations, the exposed pulp of the tooth is 2.5 mm-4 mm in occlusal depth, 3.5 mm-5 mm in mesio-distal width, and 2.5 mm-3.5 mm in faciolingual width.

In some implementations, the dental composition is in the form of a cream, a gel, or a paste.

In some implementations, the dental composition comprises a weight percent of betamethasone of 0.01%-0.2% relative to a total weight of the dental composition.

In some implementations, the dental composition comprises a weight percent of gentamicin of 0.05%-0.2% relative to a total weight of the dental composition.

In some implementations, the calcification is a dentin bridge with a thickness of 2 μm-80 μm.

In some implementations, the dental composition further comprises Portland cement.

In some implementations, the Portland cement comprises at least two compounds selected from the group consisting of tricalcium silicate, dicalcium silicate, tricalcium aluminate, tetracalcium aluminoferrite, gypsum, calcium oxide, silicon dioxide, aluminum oxide, and ferric oxide.

In some implementations, the dental composition comprises a weight percent of Portland cement of 10%-25% relative to a total weight of the dental composition.

In some implementations, the covering comprises sealing the dental composition such that the dental composition is retained in a region of the exposed pulp.

In some implementations, the glass ionomer cement is a self-curing glass ionomer cement or a resin-modified glass ionomer cement.

In some implementations, the self-curing glass ionomer cement or resin-modified glass ionomer cement is cured by light to seal the dental composition in the region of the exposed pulp.

According to a second aspect, the present disclosure relates to a dental composition having a betamethasone, a gentamicin, and a Portland cement. The dental composition forms a calcification over an exposed pulp when administered to the exposed pulp of a tooth.

In some embodiments, the dental composition is in the form of a cream, a gel, or a paste.

In some embodiments, the dental composition comprises a weight percent of betamethasone of 0.01%-0.2% relative to a total weight of the dental composition.

In some embodiments, the dental composition comprises a weight percent of gentamicin of 0.05%-0.2% relative to a total weight of the dental composition.

In some embodiments, the calcification is a dentin bridge with a thickness of 2 µm-80 µm.

In some embodiments, the dental composition further comprises Portland cement.

In some embodiments, the Portland cement comprises at least two compounds selected from the group consisting of tricalcium silicate, dicalcium silicate, tricalcium aluminate, tetracalcium aluminoferrite, gypsum, calcium oxide, silicon dioxide, aluminum oxide, and ferric oxide.

In some embodiments, the dental composition comprises a weight percent of Portland cement of 10%-25% relative to a total weight of the dental composition.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 3A is a photomicrograph of histologic sections from a specimen treated by MTA showing a dentin bridge formation over the pulp;

FIG. 3B is a magnified photomicrograph of histologic sections from a specimen treated by MTA showing a dentin bridge formation over the pulp;

FIG. 3C is a photomicrograph of histologic sections from a specimen treated by MTA showing a diffuse calcification formation over the pulp;

FIG. 3D is a magnified photomicrograph of histologic sections from a specimen treated by MTA showing a diffuse calcification formation over the pulp;

FIG. 3E is a photomicrograph of histologic sections from a specimen treated by betamethasone/gentamicin cream, showing no dentin bridge formation over the pulp;

FIG. 3F is a photomicrograph of histologic sections from a specimen treated by betamethasone/gentamicin cream, showing partial dentin bridge formation over the pulp;

FIG. 3G is a photomicrograph of histologic sections from a specimen treated by betamethasone/gentamicin cream, showing inflammatory cells over the pulp;

FIG. 3H is a photomicrograph of histologic sections from a specimen treated by betamethasone/gentamicin cream, showing pulpal abscess formation;

FIG. 4A is a micro-CT image from specimen treated by MTA in the coronal place showing the exposure site, the MTA, and the dentin bridge formation;

FIG. 4B is a micro-CT image from specimen treated by MTA in the axial plane showing MTA in the exposure site;

FIG. 4C is a micro-CT image from specimen treated by MTA in the axial plane showing MTA and the dentin bridge formation;

FIG. 4D is a micro-CT image from specimen treated by MTA in the axial plane showing the dentin bridge formation:

FIG. 4E is a micro-CT image from specimen treated by MTA in the axial plane showing the end of the dentin bridge formation:

FIG. 4F is a is a micro-CT image from specimen treated by betamethasone/gentamicin cream in the coronal place showing the exposure site, the BG cream, and the calcified mass formation;

FIG. 4G is a micro-CT image from specimen treated by betamethasone/gentamicin cream in the axial plane showing an edge of the betamethasone/gentamicin cream in the exposure site FIG. 4H is a micro-CT image from specimen treated by betamethasone/gentamicin in the axial plane showing the calcified mass formation;

FIG. 4I is a micro-CT image from specimen treated by betamethasone/gentamicin in the axial plane showing the calcified mass formation; and FIG. 4J is a micro-CT image from specimen treated by betamethasone/gentamicin in the axial plane showing the end of the calcified mass formation.

DETAILED DESCRIPTION OF THE EMBODIMENTS

Figure 1:
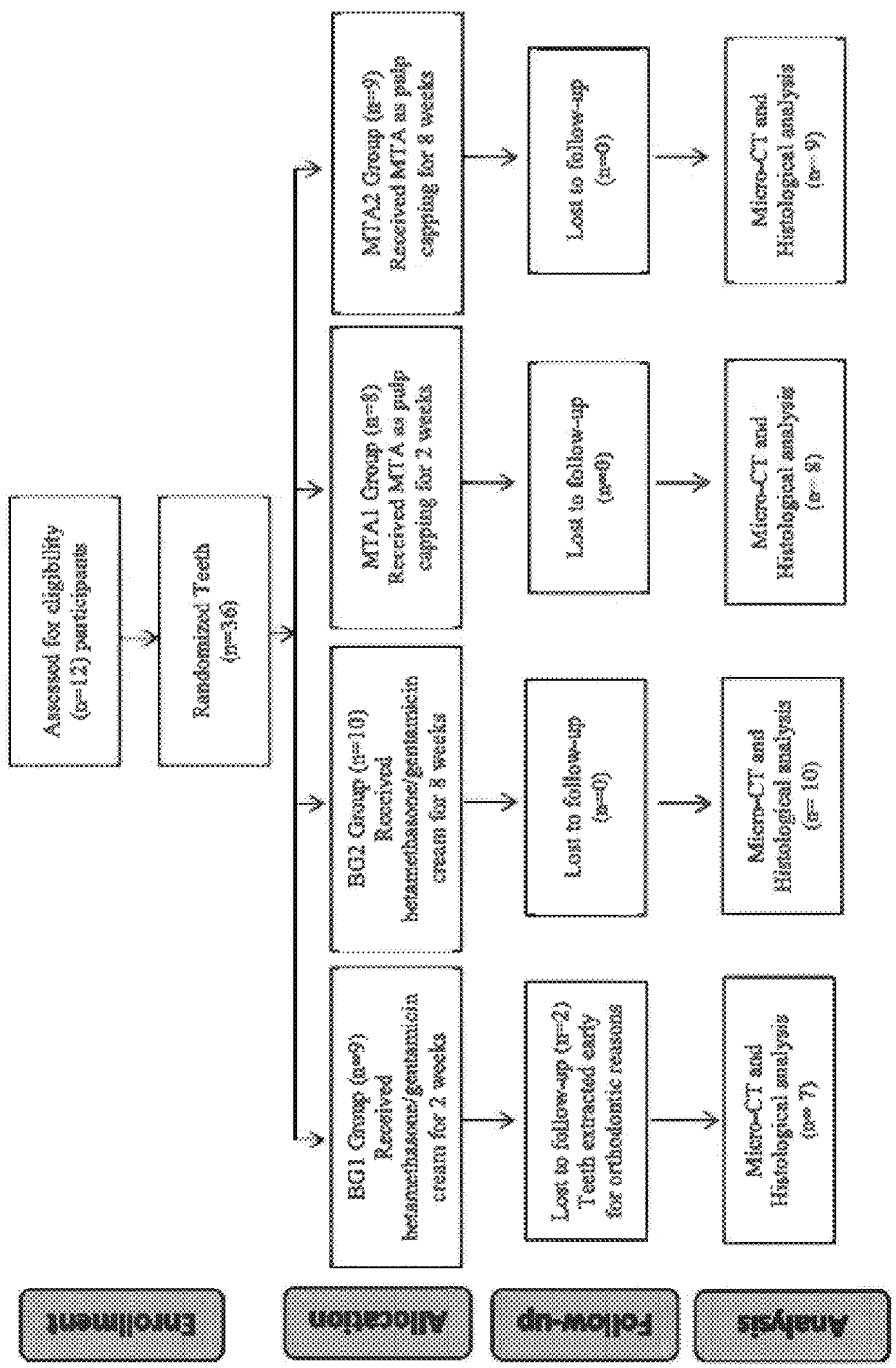
FIG. 1 is a schematic chart of the participants in the trials employed in the demonstration of the presently disclosed dental composition.

Details of the present disclosure are an extension of a published report by AlShwaimi, Emad et al. "Pulpal Responses to Direct Capping with Betamethasone/Gentamicin Cream and Mineral Trioxide Aggregate: Histologic and Micro-Computed Tomography Assessments," Journal of Endodontics, Volume 42, Issue 1, 30-35.

An aspect of the present disclosure relates to a method of direct pulp capping of a tooth by administering a dental composition onto an exposed pulp of a tooth and covering the dental composition present on the tooth with glass ionomer cement. The dental composition has betamethasone, a topical corticosteroid, and gentamicin, an antibiotic.

The dental composition may be administered in an amount effective to form a calcification over the exposed pulp of the tooth.

A dentist who has assessed a pulp exposed region of a tooth may administer the dental composition in an amount sufficient to cover the pulp exposed region. Pulp exposed regions results from the progressive spread of dental caries (i.e. cavities/decay). For example, the pulp exposed region may be sufficiently covered by a volume of the dental composition of 5 µL to 10 mL, 10 µL to 5 mL, 50 µL to 2 mL, 100 µL to 1.5 mL, 250 µL to 1 mL, or 500 µL to 750 mL. Pulpitis (inflammation of the pulp) may occur in the pulp exposed region of the tooth in which bacterial infection of the pulp occurs. The dentist may administer the dental composition of the present disclosure in order to prevent or treat such infections of the teeth.

In some implementation of the method, prior to administering the dental composition, the teeth and more preferably the pulp exposed region may be treated by a 2% cyclohexidine gluconate, an antiseptic treatment for dental procedures, or the like. The teeth may be treated by 2% cyclohexidine gluconate, an antiseptic treatment for dental procedures, or the like in an amount of 100 µL to 50 mL, 500 µL to 25 mL, 750 µL to 10 mL, 1 mL to 8 mL, or 2 mL to 5 mL.

In some embodiments, the dental composition is formulated as at least one of a cream, a gel, or a paste. The cream may include, relative to the total weight of the cream, a stable emulsion of about 5%-10% or 6%-8% by weight of each of water, one or more paraffin, and a liquid polyol (e.g. glyceryl stearate, glyceryl monooleate, glyceryl rcinoleate, diethylene glycol, sorbitan monolaurate, and the like); and about 10%-15% or 12%-13% by weight of each of beeswax, fatty alcohols (e.g. cetostearyl alcohol, cetyl alcohol, stearyl alcohol, lanolin alcohol, and the like), and a dispersing agent. In one embodiment, the dispersing agent is glyceryl monostearate. The gel may include, relative to the total weight of the gel, a glycol, including glycerin and polyethylene glycol, and preferably, propylene glycol, of a weight percent of about 5%-80%, 10%-60%, or 20%-40% and a carboxyvinyl polymer (e.g. carboxypolymethylene, Lubrizol's proprietary compounds such as 971P NF, 974P NF, 71G NF, or the like) of a weight percent of about 2%-20% or 5%-15%. The paste may include, relative to the total weight of the paste, a glycerine of a weight percent of about 10%-30% or 15%-20%, and colloidal silica of a weight percent of about 20%-80%, 30%4-70%, or 40%-60%.

In some embodiments of the dental composition, the composition further comprises a fluoride source. Exemplary sources of fluoride include, but are not limited to, sodium monofluorophosphate, stannous fluoride, alkali fluorides, such as sodium fluoride, potassium fluoride, lithium fluoride, and ammonium fluoride, tin fluoride, indium fluoride, zirconium fluoride, copper fluoride, nickel fluoride, palladium fluoride, fluorozirconates, such as sodium fluorozirconate, potassium fluorozirconate, ammonium fluorozirconate, and tin fluorozirconate, fluorosilicates, fluoroborates, fluorostannites, and mixtures thereof. Organic fluorides, such as olaflur, may also be present in the dental composition. An amount of fluoride in the dental composition may be up to 10,000 ppm, up to 5,000 ppm, or up to 2,000 PPM.

In some embodiments, the dental composition may include a dentin growth factor such as an insulin-like growth factor, a transforming factor, a platelet-derived growth factor, and morphogenetic proteins. The dentin growth factor may be a weight percent in the dental composition, relative to the total weight of the dental composition, of about 0.01%-3%, about 0.1%-2.5%, about 0.5%-2%, or about 1%-1.5%. The dentin growth factor included in the dental composition may enhance the calcification process by increasing the rate of the calcification by about 2%-25%, about 5%-20%, or about 10%-15%. The dentin growth factor may enhance the calcification process by upregulating the expression of transcription factors such as RUNX2 and odontoblastic genes such as osteocalcin and dentin sialoprotein, resulting in dentin bridge formation.

In the present disclosure specific elements are not included in the method or the dental composition, such as calcium hydroxide, calcium phosphate, aloe vera, ε-polylysine, or polysaccharides.

In some implementations, the method may include administering an odontoblast prior to administering the dental composition. An odontoblast is a cell of neural crest origin that is part of the outer surface of the dental pulp, and whose biological function is dentinogenesis. Dentinogenesis is the formation of dentin, the substance beneath the tooth enamel on a crown of the tooth and a cementum on a root of the tooth. The odontoblast may be included in the dental composition, but more preferably is administered to the pulp exposed region of the tooth. The odontoblast may be administered with a syringe or an applicator. For example, the odontoblast may be grown in a three dimensional growth matrix gel or polymer, known in the art, in vitro and administered directly to the site, then the dental composition may be administered over the layer of odontoblasts, followed by covering with the glass ionomer cement.

The betamethasone included in the presently disclosed composition, is a corticosteroid that is available as a medication in the form of a pill, by injection, and as a cream. Betamethasone reduces inflammation in the body by blocking the action of chemicals in the body that cause inflammation and swelling. The betamethasone in the dental composition may prevent inflammation and swelling when contacting the exposed pulp region of the tooth. In some embodiments, the dental composition comprises a weight percent of betamethasone, relative to a total weight of the dental composition, of 0.01%-0.2% or 0.05%-0.1%. The betamethasone may be incorporated into the present composition as a pharmaceutical composition, such as, but not limited to Diprolene, Audavate, or Lotridem.

The gentamicin included in the presently disclosed composition, is an antibiotic used to treat several types of bacterial infections, which may include bone infections, endocarditis, pelvic inflammatory disease, meningitis, pneumonia, urinary tract infections, and sepsis. Gentamicin may be administered intravenously, injection into a muscle, or topically. In some embodiments, the dental composition comprises a weight percent of gentamicin of 0.05%-0.2%, or 0.1% to 0.15% relative to a total weight of the dental composition.

In some embodiments, the dental composition further comprises Portland cement. Generally, cements are used for the retention of dental work and as bases under restorations. Portland cement presents biocompatibility and provides sealing, thus forming a barrier against infections that may be generated by microorganisms. In some embodiments, the Portland cement comprises at least two compounds selected from the group consisting of tricalcium silicate, dicalcium silicate, tricalcium aluminate, tetracalcium aluminoferrite, gypsum, calcium oxide, silicon dioxide, aluminum oxide, and ferric oxide.

The at least two compounds may be present in the Portland cement, relative to the total weight of the cement, in a weight percent of 15%-80%, 25%-70%, 35%-60%, or 45%-50%. In some embodiments, the dental composition comprises a weight percent of Portland cement relative to a total weight of the dental composition of 10%-25% or 15%-20%. The Portland cement may further include a polymer selected from styrene, vinyl, acrylic, or a combination of polymers thereof. Exemplary polymers may be, but not limited to polyvinylchloride, vinyl acetate, polyvinylsiloxanes, polystyrene, acrylonitrile butadiene styrene, poly-n-butyl acrylate, poly-n-butyl methacrylate, polyethyl acrylate, poly-2-ethylhexyl acrylate, polyethyl methacrylate, polymethyl acrylate, polymethyhnethacrylate, polyhydroxyethyl methacrylate, polyhydroxyethyl vinyl sulfide, polyhydroxypropyl methacrylate, or polyisobornyl methacrylate, and the like. The polymer may be present relative to the total dental composition in the range 0.1% to 10% by weight, 0.5% to 5% by weight, or 1% to 3% by weight. The Portland cement may further include a contrast agent visible in X-ray such as $ZrO_2$ and $BaSO_4$. The contrast agent may be present, relative to the total dental composition, in the range 0.5%-3%, or 1%-2%. The contrast agent may enable a dentist to better observe the progress of the pulp capping over time and to evaluate the progress of calcification of dentin bridge formation as described herein. For example, the dentist may administer the composition and evaluate the pulp exposed region by X-ray imaging to observe whether the pulp exposed region is sufficiently covered, then the dentist may decide to add more dental composition or if the coverage is sufficient, to continue to cover the dental composition and proceed with the method. The dentist may monitor the pulp exposed region after the treatment to observe dentin formation between the pulp exposed region and the dental composition. The dentist may wait between administration and X-ray imaging 2 minutes to 15 minutes, 5 minutes to 10 minutes, or 7 minutes-8 minutes.

In some implementations, the exposed pulp of the tooth is 2.5 mm-4 mm or 3 mm-3.5 mm in occlusal depth, 3.5 mm-5 mm or 4 mm-4.5 mm in mesiodistal width, and 2.5 mm-3.5 or 2.75 mm-3 mm in faciolingual width. Occlusal is the direction towards the biting surface of the posterior teeth or relating to the surface. Mesio- or mesial is the direction towards the anterior midline in a dental arch and distal is the direction towards the gingiva beyond the tooth furthest from the anterior midline (i.e. the last tooth). Facio- or facial is the side of a tooth that is adjacent to the inside of the lips and lingual refers to the side of a tooth adjacent to the tongue or palate. These measurements may allow for the dental composition to be set into the exposed pulp region.

The coating that is placed over the dental composition in the pulp exposed region of the tooth is a glass ionomer cement. The glass ionomer cement is a dental restorative material used in dentistry for dental fillings and dental cements. These materials are based on the reaction of silicate glass powder and polyalkenoic acid, an ionomer. For example, poly(ethylene-co-methacrylic acid) is an ionomer. Exemplary polymers which may be included in the glass ionomer cement of the present disclosure, include, but are not limited to acrylic acid, maleic acid, itaconic acid, butane dicarboxylic acid, and vinyl phosphonic acid. Exemplary glasses employed in the cement may include, but is not limited to silica, alumina, lime, strontium oxide, zinc oxide, fluorite, phosphate, and soda. The weight percent of glass in the glass ionomer cement relative to the total weight of the glass ionomer cement is 25%-90%, 35%-80% 45%-70%, or 55%-60%. The weight percent of the polymer in the glass ionomer cement relative to the total weight of the glass ionomer cement is 50%-95% or 60%-80%. In some implementations, the glass ionomer cement may be used to cover the dental composition in an amount of 5 µL to 2 mL, 10 µL to 1.75 mL, 50 µL to 1.5 mL, 100 µL to 1.25 mL, 250 µL to 1 mL, or 500 µL to 750 mL. In some implementations, when Portland cement is included in the dental composition, a lesser amount of the glass ionomer cement may be used relative to when no Portland cement is included in the dental composition, such as 10%-80% less, 20%-60% less, or 30%-50% less.

In some implementations, the dental composition including Portland cement may take several minutes to harden or dry. The dental composition including Portland cement may take 1 minute-10 minutes to dry/harden, 3 minutes to 7 minutes, or 4 minutes to 6 minutes. In some implementations, the dental composition including Portland cement may need to dry or harden before the dental composition is covered by the glass ionomer cement. In some implementations, the dental composition may not need to dry or harden before covering with the glass ionomer cement.

In some implementations of the method, the dental composition may be administered in multiple layers. For example, a first layer of the dental composition, which directly contacts the pulp exposed region, may not include the Portland cement, and a second layer of the dental composition, which includes the Portland cement, may be placed over the first layer to harden or dry, then the glass ionomer cement may cover the second layer. 1-4 layers, or 2-3 layers of the dental composition, which may optionally include the Portland cement, may be administered in the method. The thickness of the dental composition between the pulp exposed region and the glass ionomer cement may be 0.3 mm-7 mm, 0.5 mm-6 mm, 1 mm-5 mm, or 2 mm-3 mm, which may be hardened/dried or non-hardened/not dry.

In some implementations, the glass ionomer cement may be a self-curing glass ionomer cement or a resin-modified glass ionomer cement. The self-curing glass ionomer may be activated by exposure to air upon application. In some implementations, the self-curing glass ionomer cement or resin-modified glass ionomer cement may be cured by light to seal the dental composition in the region of the exposed pulp. The resin modified glass ionomer cement may be cured by the combination of two components, one containing a catalyst and the other the monomer units to polymerize. Exemplary resin-modified glass ionomer cements are Panavia 21 (J. Morita, USA), Biso C&B (Bisco Dental Products, USA), and Enforce (L. D. Caulk, USA). The glass ionomer cement may be cured in UV light from 350 nm-390 nm wavelength or blue light from 400 nm-450 nm wavelength. The curing of the glass ionomer cement may take 20 seconds to 5 minutes, 45 seconds to 3 minutes, or 1.5 minutes to 2 minutes. In some implementations, the covering comprises sealing the dental composition such that the dental composition is retained in a region of the exposed pulp. The polymerization process may provide a tight seal against saliva, food particles, acids, and liquids at a temperature range of 0° C.-75° C. 5° C.-65° C., 15° C.-55° C., or 25° C.-45° C.

The calcification that forms over the exposed pulp is also known as a dentin bridge. Dentin or dentine is a calcified tissue of the body and, along with enamel, cementum, and pulp, is one of the four major components of teeth. Dentin, which is less mineralized and less brittle than enamel, is necessary for the support of enamel. The present method may form one of three dentin types: secondary dentin, reparative dentin, and peritubular dentin. Secondary dentin is formed after root formation, as in adult teeth, but may occur in youth (ages 1-14), and occurs at a much slower rate. Secondary dentin may not form at a uniform rate along the tooth, but instead may form faster along sections closer to the crown of a tooth. This development continues throughout life and may account for the smaller areas of pulp found in older individuals. Reparative dentin may be formed by replacement odontoblasts when the injury to the root or tooth is so severe that it damages a part of the primary odontoblast layer. Peritubular dentin creates the walls of dentin tubules which may assist in generating dentin. Generally, dentin rates approximately 3 on the Mohs scale of mineral hardness (1 to 10, 10 being the hardness of a diamond). In some implementations, the dentin that forms by the method described herein may have a hardness on the Mohs scale of 1 to 4 or 2 to 3. In some implementations, the calcification is a dentin bridge of a thickness of 2 µm-80 µm, 5 µm-70 µm, 10 µm-60 µm, or 20 µm-50 µm.

The administering as described herein may be completed by a variety of tools and implements known in the art of dentistry. The dental composition may be applied on to the pulp exposed region of the tooth by a blunt instrument, such as a dental spatula, or may be injected through a syringe or tool which applies pressure to extrude the dental composition into the pulp exposed region of the tooth. The administering may further include the placement of a mold or dental grafting device which enhances the repair of the pulp exposed region of the tooth. The grafting device may be configured to hold stem cells or odontoblasts, as described herein, related to the repair of pulp of a tooth or cells to stimulate the growth of dentin.

Further the covering of the dental composition present on the tooth with the glass ionomer cement may be completed by a blunt instrument, such as a dental spatula, or may be injected through a syringe or tool which applies pressure to extrude the glass ionomer cement on to the tooth.

The examples below are intended to further illustrate the method of direct pulp capping and are not intended to limit the scope of the claims.

Example 1

Materials and Methods

A randomized clinical trial was approved by the Ethical Committee of the University of Dammam, Dammam, Saudi Arabia (2011037). First premolar teeth scheduled to be extracted for orthodontic reasons were selected for this study. Teeth included in the trial were from patients between 15 and 25 years of age who had no medical or systemic conditions; teeth were also free of periodontal disease, caries, previous restorations, and had normal pulp chambers and closed apices. A pulp status was assessed with cold and electric pulp tests.

A total of 36 selected premolars were randomly divided by using a statistical randomized treatment table into 4 groups according to the materials used and the duration of follow-up; betamethasone/gentamicin group 1 (BG1 group) (n=9), BG cream with 2-week follow-up; betamethasone/gentamicin group 2 (BG2 group) (n=10), BG cream with 8-week follow-up; mineral trioxide aggregate group 1 (MTA1 group) (n=8), MTA with 2-week follow-up; and mineral trioxide aggregate group 2 (MTA2 group) (n=9), MTA with 8-week follow-up. All participants signed an informed consent form after the clinical procedure and risks involved had been thoroughly explained and all questions raised by the participants and/or their guardians had been answered.

Pulp Exposures

The pulp cavity procedures were carried out under local anesthesia and rubber dam isolation. Teeth were cleaned by using 2% chlorhexidine gluconate, and occlusal cavities were prepared with sterile half-round carbide burs by using a high-speed handpiece and sterile distilled water cooling. The prepared occlusal cavities were 3.0-3.5 mm in occlusal depth, 4.0-4.5 mm in mesiodistal width, and 3.0-3.5 mm in faciolingual width. Dimensions of the cavity were checked with a digital caliper in an attempt to standardize the cavity size. Pulp exposures were performed in the center of the pulp floor. One bur was used for each cavity. Complete hemostasis was achieved by applying gentle pressure to the exposed site with a sterile cotton pellet moistened with sterile saline. FIG. 1 depicts the entire selection scheme and organization of the clinical assessment. BG cream was applied as a pulp-capping material in groups BG1 and BG2, and MTA was applied as a pulp-capping material according to the manufacturer's instructions in groups MTA1 and MTA2 (FIG. 1). After application of the assigned material, cavities were sealed immediately with posterior glass ionomer. All participants were instructed to record postoperative pain by using a visual analogue scale on a form provided. Teeth were extracted after 2 weeks in groups BG1 and MTA1 and after 8 weeks in groups BG2 and MTA2. The apices of extracted teeth were removed under water cooling to facilitate formalin penetration. Teeth were fixed in 10% formalin for 24 hours.

Micro-Computed Tomography

All fixed teeth were scanned with a micro-computed tomography (micro-CT) machine (SkyScan1172 version 1.5; Bruker Micro-CT, Kontich, Belgium). Each sample was positioned in the middle of the specimen stage and scanned at 70 kV and 139 mA with a resolution of 8.99 mm, rotational step of 0.25, and 360 rotations by using 0.5-mm aluminum and copper filters. Raw data were reconstructed with NRecon Software version 1.6.4.8 (Bruker Micro-CT) to obtain rough measurements of the thickness of the reparative hard tissue. Raw data were analyzed with CT analyzer (CTan) Software version 1.11.10. Two-dimensional slices were acquired in the axial plane to determine the first and last slices in the coronal-to-apical direction from which reparative hard tissues could be identified from the pulp. Data Viewer software version 1.4.4 was used to obtain 3 distinct views (coronal, sagittal, and transaxial) of each image in 2-dimensional form. This provided a precise and clear picture of each specimen and allowed measurement of the dentin bridges.

Histologic Sample Preparation

After the micro-CT scanning, fixed teeth were decalcified with 10% formic acid and sodium citrate. Teeth were split into 2 longitudinal sections at the level of pulp exposure, and each section was dehydrated in a series of ethanol solutions at ratios increasing from 45% to absolute. Samples were cleaned with xylene and embedded in paraffin. Sections 6 mm thick were prepared from each block. Ten serial sections were taken at the level of exposure. sections were stained with hematoxylin-eosin and Masson trichrome. After the sections were stained, coverslips were applied with mounting medium. Stained sections were evaluated under light microscopy by an observer blinded to the treatment according to a predesigned histopathologic protocol that included examination of the following: pulp pathology, including inflammation (type and intensity); pulp abscess and pulp necrosis; and reparative reaction of the pulp, including formation of dentin bridges. Thickness of dentin bridges was measured in micrometers at 3 random areas of each section by using Olympus cellSens Dimension V1.9 Software (Olympus, Tokyo, Japan). The mean of all measurements was recorded and used for analysis. In the present study, we considered dentin bridge formation to be a sign of healing. Data were analyzed by one-way analysis of variance and the Tukey-Kramer multiple comparison test at a significance level of P<0.05.

Results

Figure 2:
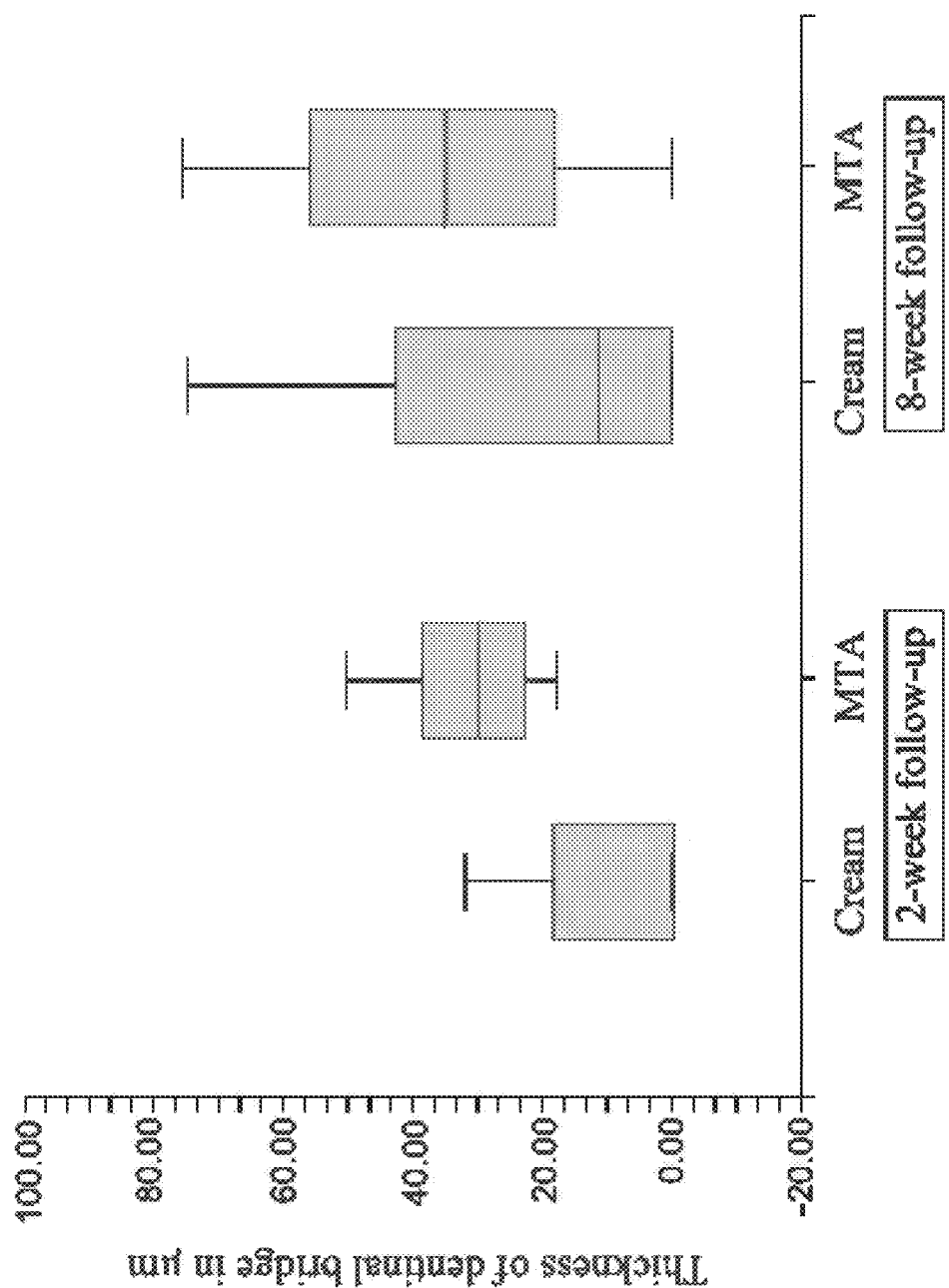
FIG. 2 is a box plot of the thickness of dentin measured in treated pulp exposed regions of a tooth.

Out of 12 participants included in this randomized clinical trial, 10 were female, and 2 were male; their average age was 18 years. Two teeth were excluded from the study because they were extracted for orthodontic reasons before completion of the study. Table 1 presents the summary of results for all groups, and FIG. 2 shows a box plot of dentin bridge thicknesses in micrometers.

TABLE 1

Summary of Findings among All Cases of Groups

| Groups | Materials | Time interval (wk) | Dentinal bridge (μm) | Abscess (%) | Type of inflammation |
|---|---|---|---|---|---|
| BG1 | BG cream | 2 | 7.19 | 14.3 | Acute type with predominant neutrophils |
| BG2 | BG cream | 8 | 22.0 | 20 | |
| MTA1 | MTA | 2 | 31.04 | 0 | |
| MTA2 | MTA | 8 | 78.50 | 11 | |

BG Cream

In BG1 group (BG cream after 2 weeks), histologic examination revealed evidence of a partial hard tissue barrier in 28.6% of the specimens; no hard tissue (dentin bridge 302) formation was apparent in 71.4% of the specimens. FIG. 3G and FIG. 3H depict the use of BG cream in the development of dentin 302 (or DB) and show encroachment of inflammatory cells 306 and an abscess in the pulp 307. The average hard tissue thickness was 7.19 mm (Table 1). In BG2 group (BG cream after 8 weeks), histologic examination revealed dentin bridge formation in 50% of the specimens. Bridge formation was complete in 10% of the specimens; hard tissue apposition at the exposure site 304 was partial or incomplete in the others. The average thickness of reparative hard tissue was 22.0 mm (FIG. 2). Micro-CT images confined the histologic results for dentin bridge 302 formation in both groups (FIG. 4A through FIG. 4J). Mild to moderate inflammatory cell infiltration was seen in all teeth in BG1 and BG2 groups. Further the DB 302 is depicted in FIG. 4C, FIG. 4D, and FIG. 4E as the micro-CT is sectioned deeper into the tooth. Similarly, in FIG. 4F through FIG. 4J, the BG cream application 402 is shown and the calcified mass (CM) 403 is shown as a likely precursor to dentin bridge formation. Inflammatory cell infiltration in all cases was of the acute type, with neutrophils predominating. Pulp abscesses developed in 1 tooth in BG1 group (14%) and in 2 teeth in BG2 group (20%) (Table 1). Dentin bridges did not appear in any teeth with pulp abscesses in which the tissue underwent necrotic changes.

MTA

In MTA1 group (MTA after 2 weeks), histologic examination revealed dentin bridge formation in 100% of the specimens. The average hard tissue thickness was 31.04 mm. In MTA2 group (MTA after 8 weeks), dentin bridge formation at the exposure site was evident in 89% of the specimens. The average thickness of reparative hard tissue was 78.50 mm (Table 1). A complete dentin bridge with normal structure had formed in 67% of the specimens; a partial or incomplete hard tissue barrier had formed at the exposure site in the remaining 23%. Hard tissue that formed at the exposure site took the form of diffuse calcification in 4 samples treated with MTA. FIG. 3A through FIG. 3F depict the use of MTA 305 in the exposure site 304 and the growth of diffuse calcification (DC) 301 or dentin bridge (DB) 302 between the pulp 303 and the exposure site 304 Micro-CT images confirmed the histologic results for dentin bridge formation. FIG. 4A-FIG. 4E depict the Micro-CT images of teeth having the MTA treatment. FIG. 4A and FIG. 4B depict the MTA 305 and the area where DB form 302.

Mild to moderate inflammatory cell infiltration was seen in 80% of the specimens in MTA1 and MTA2 groups. As with the teeth in the BG1 and BG2 groups, inflammatory cell infiltration in all cases was of the acute type, with neutrophils predominating. A pulp abscess developed in 1 tooth in ITA2 group (1%) (Table 1). A dentin bridge was not apparent in the tooth with the pulp abscess.

Statistical Comparison

The thickness of the dentin bridge differed significantly among the experimental groups (P<0.05); the dentin bridge was thicker in group 4 than in groups 1, 2, or 3 (P<0.05). The differences in dentin bridge thickness between groups 1 and 2 and between groups 3 and 4 were also statistically significant (both P<0.05).

No statistically significant differences in the distribution of inflammatory cell infiltrates were found among the groups (P>0.05). Mild pain lasting for 1-3 days was associated with 12% of the exposed teeth; severe pain lasting for 3 days was associated with 6% of the exposed teeth.

Dentin bridge formation at the interface of pulp and capping material could be either a sign of healing or a reaction to irritation. This may be a controversial issue because a dentin bridge does not prove that the pulp is healthy or protects it from bacterial challenges. Most previous direct pulp-capping studies used animal models (rats, dogs, or baboons). Although the pulpal tissues of these species closely resemble those of humans, studies evaluating the responses of human pulpal tissue to direct pulp-capping materials are preferable. Therefore, an evaluation of the response of pulp tissue to BG cream and MTA used as direct pulp-capping materials in human teeth was important to the field.

Pulpal responses in this study were evaluated with both micro-CT and light microscopy. The micro-CT technique allowed for high resolution scanning of extracted teeth to provide further information about the quality of the newly formed reparative hard tissue as compared with previous studies, where portions of animal jaws were scanned at low resolution. In addition, histologic sections were viewed under a light microscope, and software was used to measure the dimensions of newly formed hard tissue barriers to the micrometer.

Topical application of glucocorticoid-antibiotic combination has been infrequently used for the treatment of skin diseases and ear infections without unwanted drug interactions. BG cream has been proposed as a direct pulp-capping material because of its antimicrobial and anti-inflammatory effects. However, the present study did not show that BG produced results better than those of MTA.

In the present study, BG cream resulted in dentin bridge formation in only 29% and 50% of specimens after 2 and 8 weeks, respectively. Although the dentin bridge was significantly thicker after 8 weeks than after 2 weeks, it was only partially formed at both observation times. In a previous study on rabbits, direct pulp capping with BG cream under calcium hydroxide significantly reduced the histologic changes indicating an inflammatory response, as compared with calcium hydroxide alone. However, to our knowledge, no other published studies have evaluated the efficacy of BG cream as a direct pulp capping material in humans. Pulpal responses were evaluated at 8 weeks because this time interval was used in a number of previous studies. Pulpal responses were also evaluated at an earlier time because the initiation of hard tissue formation has been reported to start as early as 2 weeks. A variety of direct pulp-capping materials can reportedly initiate dentin bridge formation at the exposure site. Previous studies that used animal and human models reported that direct pulp capping with MTA initiated tertiary dentin formation more effectively than capping with other materials. These findings are in agreement with those of the present study, in which MTA performed significantly better than BG cream.

Direct pulp capping with MTA results in the formation of fibrodentin and reparative dentin at the pulpal surface. After initial contact, a superficial crystalline layer is formed on the exposed pulp surface, followed by formation of a lining of columnar odontoblast-like cells. After MTA hardens, it forms calcium oxide that may react with tissue fluids to form calcium hydroxide. The mechanism of action of MTA may thus be similar to that of calcium hydroxide.

However, MTA is more effective than calcium hydroxide because it promotes the differentiation of pulpal cells into odontoblast-like cells by upregulating the expression of transcription factors such as RUNX2 and odontoblastic genes such as osteocalcin and dentin sialoprotein, resulting in dentin bridge formation. Hard tissue may form adjacent to MTA because of its high alkalinity, sealing ability, and biocompatibility. In the present study, hard tissue formation was observed in all teeth capped with MTA after 2 weeks, with mild to moderate inflammation. In comparison, only 28.6% of the teeth capped with BG cream showed evidence of partial hard tissue formation. The findings are in agreement with previous studies that also demonstrated hard tissue formation 2 weeks after capping with MTA. The difference in dentin bridge formation at 2 and 8 weeks in the 2 MTA group was statistically significant. At 8 weeks, the hard tissue formation at the exposure site was thicker, with less inflammation. However, a thinner hard tissue barrier was also observed in all specimens at 2 weeks. Pulp capping with MTA may have initiated the formation of hard tissue at 2 weeks. This tissue would gradually be lined by odontoblast-like cells and become calcified in a tubular pattern, forming a thicker dentin bridge. The data confirmed the results reported in previous studies of pulp capping with MTA. Diffuse calcification was found in pulpal tissue not adjacent to the capping material in 4 teeth in the MTA group. The reason was unknown, however, the mechanism may be similar to that of pulp stone formation. Because BG is a cream, it dissolves in tissue fluids and does not provide a solid surface, whereas MTA sets to a hard structure even in the presence of moisture, providing a solid base and sealing ability. High solubility and fast dissolution are also drawbacks for conventional calcium hydroxide in reparative dentinogenesis. Both MTA and BG caused mild to moderate acute pulpal inflammation with predominantly neutrophilic infiltrates in all groups. Although a previous study reported that betamethasone cream was an effective and biocompatible direct pulp-capping material in an animal model, we found pulpal necrosis and abscesses in 3 teeth capped with BG but in only 1 tooth capped with MTA.

The invention claimed is:

1. A method of direct pulp capping of a tooth comprising:
   administering a dental composition consisting of betamethasone, gentamicin, water, a paraffin, a liquid polyol, beeswax, a fatty alcohol, and a dispersing agent onto an exposed pulp of the tooth;
   covering the dental composition present on the tooth with a glass ionomer cement; and
   curing the glass ionomer cement to form a cured glass ionomer cement and to seal the dental composition in the region of the exposed pulp;
   wherein the dental composition is administered in an amount effective to form a calcification over the exposed pulp.

2. The method of claim 1, wherein the exposed pulp of the tooth is 2.5 mm-4 mm in occlusal depth, 3.5 mm-5 mm in mesiodistal width, and 2.5 mm-3.5 mm in faciolingual width.

3. The method of claim 1, wherein the dental composition is in the form of a cream.

4. The method of claim 1, wherein the calcification is a dentin bridge with a thickness of 2 µm-80 µm.

5. The method of claim 1, wherein the glass ionomer cement is a self-curing glass ionomer cement or a resin-modified glass ionomer cement.

6. The method of claim 5, wherein the self-curing glass ionomer cement or resin-modified glass ionomer cement is cured by light to seal the dental composition in the region of the exposed pulp.

7. The method of claim 1, wherein the dental composition is administered onto the exposed pulp of the tooth forming a layer of the dental composition having a thickness of 0.3-7 mm.

8. The method of claim 1, wherein the glass ionomer cement is a reaction product of a silicate glass powder and a poly(ethylene-co-methacrylic acid) ionomer.

9. The method of claim 8, wherein a weight percent of the silicate glass powder in the glass ionomer cement is 25-35%, relative to a total weight of the glass ionomer cement.

10. The method of claim 1, which forms a layered structure consisting of the tooth, a layer of the dental composition, and a layer of the cured glass ionomer cement, wherein the layer of the dental composition is disposed between the tooth and the layer of the cured glass ionomer cement.

* * * * *